US008512309B2

(12) United States Patent
Shemesh et al.

(10) Patent No.: US 8,512,309 B2
(45) Date of Patent: Aug. 20, 2013

(54) VIAL ADAPTER ELEMENT

(75) Inventors: Eli Shemesh, Ashdod (IL); Amos Shapira, Kibbutz Gal On (IL)

(73) Assignee: Teva Medical Ltd., Ashdod (IL)

( * ) Notice: Subject to any disclaimer, the term of this patent is extended or adjusted under 35 U.S.C. 154(b) by 717 days.

(21) Appl. No.: 12/354,004

(22) Filed: Jan. 15, 2009

(65) Prior Publication Data

US 2010/0179506 A1 Jul. 15, 2010

(51) Int. Cl.
*A61M 5/32* (2006.01)

(52) U.S. Cl.
USPC ............................ 604/414; 604/411; 141/329

(58) Field of Classification Search
USPC .................................. 604/411–414; 141/329
See application file for complete search history.

(56) References Cited

U.S. PATENT DOCUMENTS

| | | | | | |
|---|---|---|---|---|---|
| 4,128,098 | A * | 12/1978 | Bloom et al. | 604/406 |
| 4,675,020 | A * | 6/1987 | McPhee | 604/411 |
| 4,759,756 | A | 7/1988 | Forman et al. | |
| 5,122,123 | A * | 6/1992 | Vaillancourt | 604/192 |
| 5,269,771 | A * | 12/1993 | Thomas et al. | 604/539 |
| 5,279,576 | A * | 1/1994 | Loo et al. | 604/187 |
| 5,304,163 | A * | 4/1994 | Bonnici et al. | 604/403 |
| 5,344,417 | A * | 9/1994 | Wadsworth, Jr. | 604/414 |
| 5,641,010 | A * | 6/1997 | Maier | 141/329 |
| 5,647,845 | A * | 7/1997 | Haber et al. | 604/32 |
| 5,890,610 | A * | 4/1999 | Jansen et al. | 215/253 |
| 5,989,237 | A * | 11/1999 | Fowles et al. | 604/413 |
| 6,019,750 | A * | 2/2000 | Fowles et al. | 604/403 |
| 6,022,339 | A * | 2/2000 | Fowles et al. | 604/411 |
| D472,316 | S * | 3/2003 | Douglas et al. | D24/129 |
| 6,558,365 | B2 * | 5/2003 | Zinger et al. | 604/410 |
| 6,685,692 | B2 * | 2/2004 | Fathallah | 604/411 |
| 6,715,520 | B2 * | 4/2004 | Andreasson et al. | 141/329 |
| 6,875,205 | B2 * | 4/2005 | Leinsing | 604/414 |
| 7,452,348 | B2 * | 11/2008 | Hasegawa | 604/411 |
| 7,648,491 | B2 * | 1/2010 | Rogers | 604/414 |
| D616,984 | S * | 6/2010 | Gilboa | D24/129 |
| 2002/0127150 | A1 * | 9/2002 | Sasso | 422/103 |
| 2002/0128628 | A1 * | 9/2002 | Fathallah | 604/411 |
| 2003/0153895 | A1 * | 8/2003 | Leinsing | 604/403 |
| 2005/0148994 | A1 * | 7/2005 | Leinsing | 604/414 |
| 2007/0106244 | A1 | 5/2007 | Mosler et al. | |
| 2008/0177244 | A1 * | 7/2008 | Capitaine et al. | 604/414 |
| 2009/0177177 | A1 * | 7/2009 | Zinger et al. | 604/414 |
| 2009/0177178 | A1 * | 7/2009 | Pedersen | 604/414 |

FOREIGN PATENT DOCUMENTS

WO WO91/05581 5/1991

* cited by examiner

*Primary Examiner* — Susan Su

(74) *Attorney, Agent, or Firm* — Dekel Patent Ltd; David Klein

(57) ABSTRACT

A vial adapter element for use in a drug mixing system including a body, a vial connection port extending from the body, a hollow vial puncturing spike that protrudes into the vial connection port and is in fluid communication with a syringe-adapter-element connection port that extends from the body, and a plurality of resilient tongues spaced around an inner wall of the body, the tongues being located in gaps formed in the inner wall of the body.

11 Claims, 4 Drawing Sheets

VIAL ADAPTER ELEMENT

FIELD OF THE INVENTION

The present invention relates to drug mixing systems generally and particularly to a vial adapter with improved connection features for connecting thereto a vial.

BACKGROUND OF THE INVENTION

Drug mixing systems are well known in the art. One particular drug mixing system is described in published PCT patent application WO 2005/041846, assigned to the current assignee of the present application, the disclosure of which is incorporated herein by reference. The drug mixing system is commercially available from Teva Medical Ltd. and is sold under the brand name Tevadaptor. It is a system for safe compounding and administration of hazardous intravenous drugs. Tevadaptor minimizes the risk of exposure to hazardous drug substances, and eliminates the risk of needle stick injuries. The drug mixing system is intended for use with a luer fitted syringe, and is particularly useful for handling toxic drugs such as antineoplastic drugs.

The Tevadaptor drug mixing system includes a receptacle port adapter that can be inserted into a port of a fluid receptacle, such as an IV bag. A vial adapter element is provided for connection to a vial containing a drug. A syringe adapter element may be attached to a syringe and to the receptacle port adapter and/or the vial adapter element. The receptacle port adapter, syringe adapter element and/or the vial adapter element may be vented to the atmosphere in a manner that prevents release to the atmosphere of possibly harmful contents of the vial in a liquid, solid or gaseous form.

The syringe adapter element may have a needle that fluidly communicates with the contents of the syringe. The needle does not normally protrude outwards, but rather is sealed inside the syringe adapter element by a septum. The syringe adapter element may be screwed onto the luer lock tip of the syringe. The needle of the syringe adapter element is now in fluid communication with the contents of the syringe.

Similarly, the vial adapter element may have a spike that fluidly communicates with the contents of the vial, and is sealed by a septum. The vial may be pushed onto the vial adapter element, wherein the spike of the vial adapter element punctures the septum of the vial. The vial adapter element may then be pushed onto the syringe adapter element, wherein the needle of the syringe adapter element punctures the septa of the syringe adapter element and the vial adapter assembly. This allows fluid to flow from the syringe through the needle of the syringe adapter element and through the spike of the vial adapter element to the vial.

After filling the vial with a desired amount of fluid, the vial adapter assembly may be separated from the syringe adapter element. During separation, the needle of the syringe adapter element is sealed by elastomeric septa. In this manner, no fluid drips outwards.

SUMMARY OF THE INVENTION

The present invention seeks to provide further features to a drug mixing system, particularly a vial adapter with improved connection features for connecting thereto a vial, as is described further in detail hereinbelow.

There is thus provided in accordance with an embodiment of the present invention a vial adapter element for use in a drug mixing system including a body, a vial connection port extending from the body, a hollow vial puncturing spike (optionally mounted in a counterbore formed in the body) that protrudes into the vial connection port and is in fluid communication with a syringe-adapter-element connection port that extends from the body, and a plurality of resilient tongues spaced around an inner wall of the body, the tongues being located in gaps formed in the inner wall of the body (e.g., each tongue optionally including a cantilevered arm that terminates in a chamfered lug). A biasing device may be optionally placed in the counterbore for creating a biasing force towards the resilient tongues.

In accordance with an embodiment of the present invention the body includes an outwardly extending proximal rim. The cantilevered arms may extend along the inner wall of the body. The cantilevered arms may be as thick as the inner wall of body, and the chamfered lugs may be thicker than the cantilevered arms.

In accordance with an embodiment of the present invention each chamfered lug extends radially towards a center of the body and is located at a proximal end of a cutout formed in the body.

In accordance with an embodiment of the present invention the biasing device includes a coil spring. Alternatively, in accordance with another embodiment of the present invention the biasing device includes a flexible cylindrical element having a hole for the spike to pass therethrough.

In accordance with another embodiment of the present invention the body includes a conical flange that extends inwards from the rim. Each cantilevered arm may depend from a proximal end of a cutout formed in the conical flange, and an appendage may extend from a distal edge of the cantilevered arm from which extends the chamfered lug.

In accordance with another embodiment of the present invention each cantilevered arm may extend from a floor of the body and may be located in a cutout formed in the body, and an appendage may extend from a distal edge of the cantilevered arm from which extends the chamfered lug.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
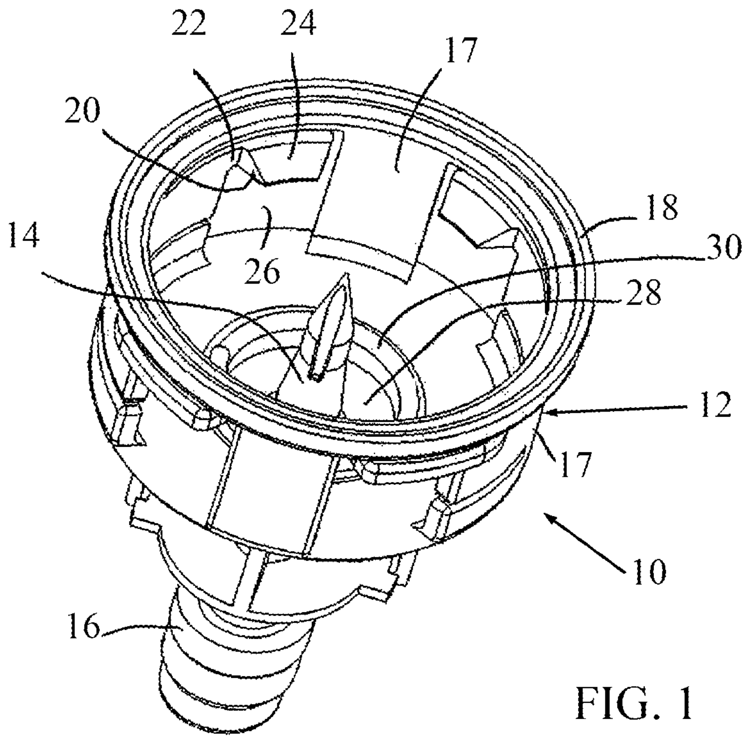
FIG. 1 is a simplified illustration of a vial adapter element, constructed and operative in accordance with an embodiment of the present invention.

Reference is now made to FIG. 1, which illustrates a vial adapter element 10, constructed and operative in accordance with an embodiment of the present invention. Vial adapter element 10 may be made of any suitable sturdy material, such as a medically safe metal or plastic.

Vial adapter element 10 may include a vial connection port 12, described in detail below. A hollow vial puncturing spike 14 protrudes into the middle of vial connection port 12. Spike 14 sits in a counterbore 28, which can be integrally molded as part of body 17, for example.

Spike 14 is in fluid communication with syringe-adapter-element connection port 16. As is known in the art, such as in PCT patent application WO 2005/041846, syringe-adapter-element connection port 16 includes a hollow tubular portion (not shown) in fluid communication with spike 14. The tubular portion is covered at an end opposite to spike 14 with a septum (not shown). A syringe adapter element (not shown) has a needle and can be pushed on to syringe-adapter-element connection port 16, whereupon the needle of the syringe adapter element punctures the septum of the tubular portion of port 16, This effects fluid communication between the syringe adapter element and spike 14 so that contents (e.g., a drug in liquid solution) of a syringe (not shown) connected to the syringe adapter element can flow to spike 14 and from there into a vial (not shown) that has previously been connected to vial connection port 12.

In the embodiment illustrated in FIG. 1, vial connection port 12 includes a body 17 (typically shaped as a circular cup) with a proximal (proximal meaning closest to the vial that will be connected to port 12) rim 18 that extends outwards from body 17. A plurality of resilient tongues 20 are spaced around the inner wall of body 17. Each tongue 20 is constructed of a cantilevered arm 22 that extends along the inner wall of body 17 and terminates in a chamfered lug 24. The cantilevered arm 22 can be the same thickness as the wall of body 17 (or alternatively of a different thickness, but flush with the outer surface of the wall), whereas the chamfered lug 24 is thicker than cantilevered arm 22. Each chamfered lug 24 extends radially towards the center of body 17 (that is, towards the spike 14) and is located at a proximal end of a cutout 26 formed in body 17. Tongues 20 may be equally spaced around the body 17, or alternatively, may be unequally spaced there around.

When a vial is pushed into vial connection port 12, the neck of the vial initially contacts the chamfered lug 24 and pushes them radially outwards as the neck of the vial pushes past them. The chamfered lugs 24 can be more resilient, less resilient or just as resilient in the radially outward direction (perpendicular to spike 14) compared with the axial direction (parallel to spike 14), by appropriately designing the moment of inertia of cantilevered arm 22 to be either greater, smaller or equal in the radially outward direction compared with the axial direction, respectively After pushing the vial into vial connection port 12, spike 14 punctures a septum of the vial and the vial head goes into the inner diameter of the wall of body 17. In order to compensate for any mismatch in tolerances when connecting the vial to port 12, a biasing device 30 is placed in counterbore 28. Biasing device 30 urges the vial against chamfered lugs 24 of tongues 20, thereby ensuring minimal residual volume when the contents are emptied from the vial. In the embodiment illustrated in FIG. 1, biasing device 30 is a coil spring, made of a safe material, such as metal, elastomer, sponge, foam or plastic or any combination thereof.

Figure 2:
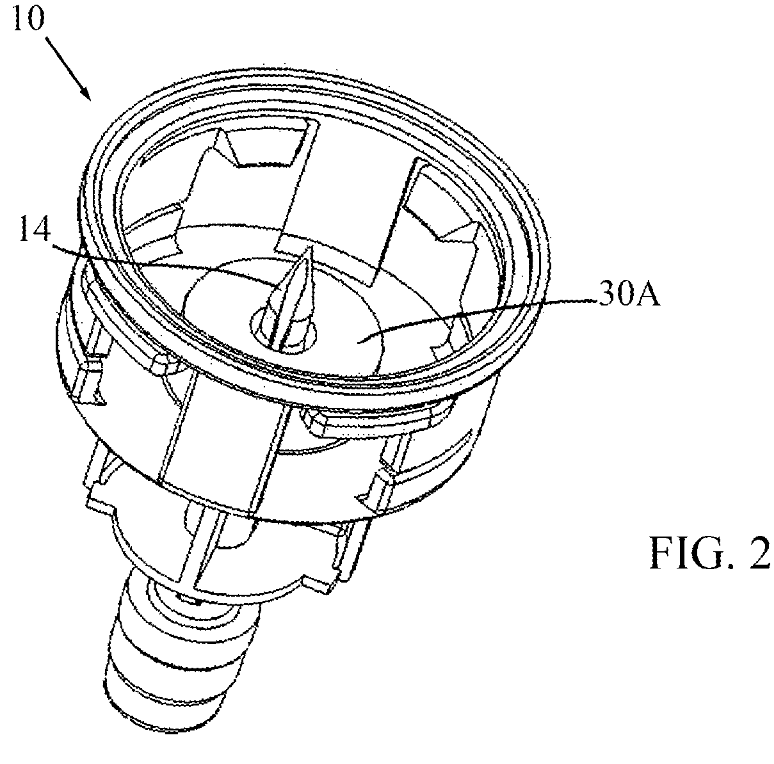
FIG. 2 is a simplified illustration of a vial adapter element, constructed and operative in accordance with another embodiment of the present invention.

Reference is now made to FIG. 2, which illustrates another version of vial adapter element 10. In this version, vial adapter element 10 includes a biasing device 30A which is a flexible cylindrical element having a hole for spike 14 to pass therethrough. The biasing device 30A may be made of a safe elastomer (e.g., rubber, silicone rubber and the like) or a foam (e.g., silicone rubber foam and the like).

Figure 3:
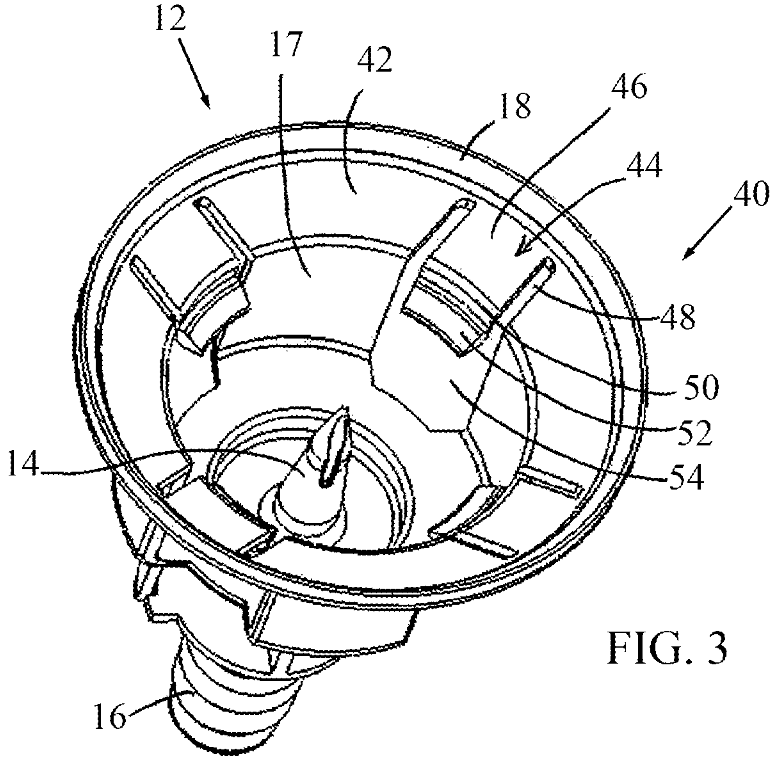
FIG. 3 is a simplified illustration of a vial adapter element, constructed and operative in accordance with yet another embodiment of the present invention.

Reference is now made to FIG. 3, which illustrates a vial adapter element 40, constructed and operative in accordance with another embodiment of the present invention. Vial adapter element 40 is similar to vial adapter element 10, with like elements being designated by like numerals. Vial adapter element 40 differs from vial adapter element 10 in the structure of the resilient tongues used to secure the vial pushed therein. Body 17 includes a conical flange 42 that extends inwards from rim 18. A plurality of resilient tongues 44 are spaced around the inner wall of body 17. Each tongue 44 is constructed of a cantilevered arm 46 that depends from the proximal end of a cutout 48 formed in conical flange 42. An appendage 50 extends downwards from the distal edge of cantilevered arm 46 and terminates in a chamfered lug 52. Appendage 50 and lug 52 are situated in a cutout 54 formed in body 17.

Figure 4:
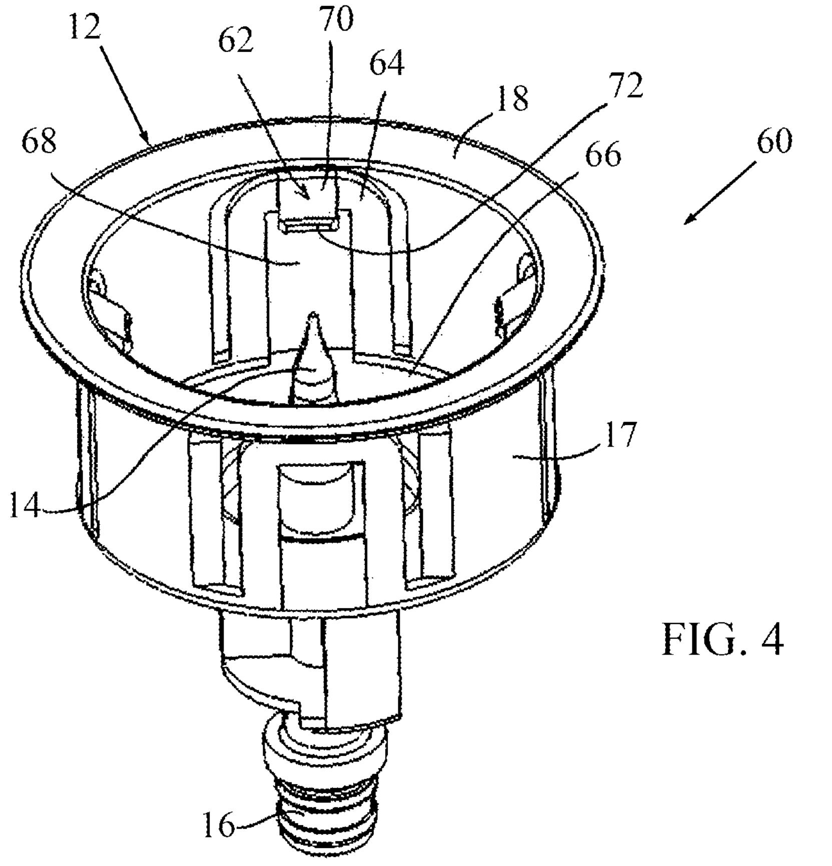
FIG. 4 is a simplified illustration of a vial adapter element, constructed and operative in accordance with still another embodiment of the present invention.

Reference is now made to FIG. 4, which illustrates a vial adapter element 60, constructed and operative in accordance with another embodiment of the present invention. Vial adapter element 60 is similar to vial adapter element 10 or 40, with like elements being designated by like numerals. Vial adapter element 60 differs from the previous embodiments in the structure of the resilient tongues used to secure the vial pushed therein. A plurality of resilient tongues 62 are spaced around the inner wall of body 17. Each tongue 62 is constructed of a cantilevered arm 64 (U-shaped in the illustrated embodiment) that extends upwards from a floor 66 of body 17 and is located in a cutout 68 formed in body 17. An appendage 70 extends downwards from the proximal edge of cantilevered arm 64 and terminates in a chamfered lug 72.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. A vial adapter element for use in a drug mixing system comprising:

a vial connection port comprising a body, said body comprising an inner wall and said vial connection port comprising a vial abutment surface extending in wards from and transverse to said inner wall;

a hollow vial puncturing spike that protrudes into said vial connection port and is in fluid communication with a syringe-adapter-element connection port that extends from said body;

a counterbore formed in said vial abutment surface;

a plurality of resilient tongues spaced around said inner wall of said body, said tongues being located in gaps formed in the inner wall of said body; and a biasing device placed in said counterbore, said biasing device protruding proximally beyond said vial abutment surface and arranged to create a biasing force towards said resilient tongues.

2. The vial adapter element according to claim 1, wherein said body comprises an outwardly extending proximal rim.

3. The vial adapter element according to claim 1, wherein each tongue comprises a cantilevered arm that terminates in a chamfered lug, and said cantilevered arms extend along the inner wall of said body.

4. The vial adapter element according to claim 1, wherein each tongue comprises a cantilevered arm that terminates in a chamfered lug, said cantilevered arms being as thick as the inner wall of said body, and wherein said chamfered lugs are thicker than said cantilevered arms.

5. The vial adapter element according to claim 1, wherein each tongue comprises a cantilevered arm that terminates in a chamfered lug, and each chamfered lug extends radially towards a center of said body and is located at a proximal end of a cutout formed in said body.

6. The vial adapter element according to claim 1, wherein said biasing device comprises a coil spring.

7. The vial adapter element according to claim 1, wherein said biasing device comprises a flexible cylindrical element having a hole for said spike to pass therethrough.

8. The vial adapter element according to claim 2, wherein said body comprises a conical flange that extends inwards from said rim.

9. The vial adapter element according to claim 8, wherein each tongue comprises a cantilevered arm that terminates in a chamfered lug, and each cantilevered arm depends from a proximal end of a cutout formed in said conical flange, and an appendage extends from a distal edge of said cantilevered arm from which extends said chamfered lug.

10. The vial adapter element according to claim 1, wherein each tongue comprises a cantilevered arm that terminates in a chamfered lug, and each cantilevered arm extends from a floor of said body and is located in a cutout formed in said body, and an appendage extends from a distal edge of said cantilevered arm from which extends said chamfered lug.

11. The vial adapter element according to claim 1, wherein said hollow vial puncturing spike is mounted in said counterbore.

* * * * *